United States Patent [19]

Nash

[11] 4,093,664

[45] June 6, 1978

[54] BIS HALOGENATED PHENOXYALKANOATES AND THE METHOD OF MAKING SAME

[75] Inventor: Lawrence H. Nash, Fort Lauderdale, Fla.

[73] Assignee: Kalo Laboratories, Inc., Kansas City, Mo.

[21] Appl. No.: 733,178

[22] Filed: Oct. 18, 1976

[51] Int. Cl.² ............... C07C 179/14; A01N 9/00
[52] U.S. Cl. .................. 260/610 D; 71/66; 71/76; 71/79
[58] Field of Search .................. 260/610 D, 610 R

[56] References Cited
FOREIGN PATENT DOCUMENTS 1,086,405 10/1967 United Kingdom ............ 260/610 D

OTHER PUBLICATIONS

Swain et al., "J. Amer. Chem. Soc." vol. 72, p. 5426.

*Primary Examiner*—James O. Thomas, Jr.
*Assistant Examiner*—Werren B. Lone
*Attorney, Agent, or Firm*—Schwartz & Weinrieb

[57] ABSTRACT

Compounds useful as plant growth regulators having the formula:

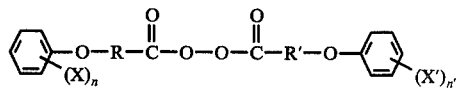

wherein X and X' are each halogens, R and R' are each alkyl groups containing from 1 to 4 carbon atoms and $n$ and $n'$ each have a value from 1 to 5. Method of preparing said compounds is also disclosed.

4 Claims, No Drawings

BIS HALOGENATED PHENOXYALKANOATES AND THE METHOD OF MAKING SAME

BACKGROUND OF THE INVENTION

The present invention relates to halogenated phenoxyalkanoates as plant growth regulators and more particularly to novel bis halogenated phenoxyalkanoates that are effective for achieving complete control, complete estermination and removal of undesired plants at a reasonable cost with the regrowth of plants treated with said novel compounds.

Halogenated phenoxyalkanoic acids are well known in the art, however, these compounds exhibit undesired harmful effects, when used in the form of emulsions, inverted emulsions, esters, ethers, esters, alkali solutions, amine salts and acetates. In addition said compounds and compositions have been found to be unstable under certain conditions as well as highly toxic to aquatic life.

Halogenated phenoxyalkanoates have also been extensively used as plant growth regulators. One such compound is 2,4-dichlorophenoxyacetic acid. The compound, as well as the alkali metal salts thereof, are slightly soluble in water. These compounds have been found to be highly toxic to aquatic life. A higher analog, the sodium salt of 2,4,5-trichlorophenoxypropionic acid, is not permitted to be used because of its toxicity.

OBJECTS OF THE INVENTION

It is therefore a significant object of the present invention to provide an effective plant growth regulator which is effective for achieving complete control, complete extermination and removal of undesired plants at a reasonable cost without harmful effects to aquatic life.

A further object of the invention is the provision of a water-insoluble plant growth regulator that is free of alkali materials, amines or any other matter that would change the plant growth regulator molecule.

A still further object of this invention is the provision of novel compounds that can be produced without the formation of side products or impurities that can have harmful effects on the plant growth regulating activities of the novel compounds of this invention.

Another object of this invention is the provision of novel compounds that exhibit a favorable rate of disappearance from the soil after application thereby avoiding residual action by remaining in the soil after the peak desired period for chemical control has passed.

Yet another object of this invention is to provide a plant growth regulator that is useful as a general plant growth regulator on lawns, golf courses, parks, playgrounds, home gardens, farms, ditches, canals, ponds, lakes, nurseries and whereever the control of plants are necessary. Consistent with this object of the invention is the further object of this invention that the compounds of this invention have no ill effect upon aquatic life nor on water so treated, especially when used for irrigation, human or animal purposes.

Still another object of this invention is the provision of new plant growth regulators that can be made readily available at reasonable prices and can be incorporated into a variety of compositions thereby facilitating its application and use.

This invention will be better understood and objects other than those set forth above will become apparent when consideration is given to the following detailed description of the invention including the various embodiments thereof.

BRIEF SUMMARY OF THE INVENTION

Briefly, the present invention relates to compounds of the formula:

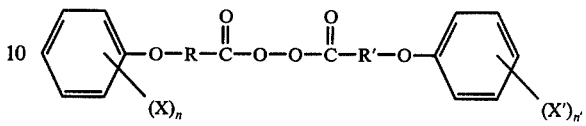

wherein X and X' are both halogen, R and R' are each alkyl groups containing from 1 to 4 carbon atoms and n and n' each have a value from 1 to 5. The present invention also relates to a method for preparing said compounds which comprises the reaction of: (a) 2 moles of at least one compound of the formula:

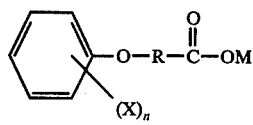

wherein M is ammonium or an alkali metal and R is an alkyl containing from 1 to 4 carbon atoms, and (b) 1 mole of a compound of the formula:

$$M'_2S_2O_8.$$

wherein M' is ammonium or an alkali metal.

DETAILED DESCRIPTION OF THE INVENTION

As noted hereinbefore, X is a halogen, the halogen generally being chlorine. The value of n and n' generally ranges from 1 to 5 and preferably has a value of 2.

Both R and R' can be the same or different alkyl groups and each alkyl group contains from 1 to 4 carbon atoms, and each preferably contains from 1 to 2 carbon atoms.

The preferred compounds of this invention are bis 2,4-dichlorophenoxyacetate and bis 2,4-dichlorophenoxypropionate.

The compounds of this invention are water-insoluble and are therefore capable of removing themselves from soil and water by means of decomposition due to soil bacteria and have been found to be non-toxic to aquatic life and small animals, yet the compounds can be made water-miscible, if so desired. Some of the plants controlled by the novel compounds of this invention include, for example, hydrilla, coontail, watermillfoil, pondweed, stinkweed, naiad, bullrush, chickweed, cockleburr, duckweed, elderberry, morning glory, mustard, waterlilly, dogfennel, pigweed and many other common weeds.

PREPARATION OF THE COMPOUNDS OF THIS INVENTION

The novel compounds can be prepared by using compound (a) as a reactant or by initially forming said compound (a) by the reaction of two moles of a halogenated, preferably chlorinated, phenoxyalkanoic acid with an equimolar amount of an aqueous solution of an alkali metal or ammonium hydroxide which is heated to a temperature sufficient to cause said halogenated phenoxyalkanoic acid to become solubilized therein just prior to the addition of said acid. The resulting reaction product which is present in solution contains a compound corresponding to compound (a), above, said compound then being reacted with an aqueous solution of 1 mole of a compound (b) wherein M is ammonium or an alkali metal, said alkali metal generally being sodium or potassium. Compound (b) is preferably ammonium persulfate and is preferably present in 1,000 ml. of water when combined with compound (a) to form the novel compounds of this invention.

In accordance with a preferred embodiment of this invention, 2 moles of 2,4-dichlorophenoxyacetic acid is initially added to a heated aqueous solution of potassium hydroxide (wherein 2 moles of potassium hydroxide is present in 1,000 ml. of water). The aqueous solution of potassium hydroxide is then heated to a temperature sufficient to cause said 2,4-dichlorophenoxyacetic acid to become soluble in said water which is generally achieved at temperatures up to about 95° C. A clear light brown solution results and 1 mole of ammonium persulfate in 1,000 ml. of water is then preferably added to the light brown solution resulting in the formation of a light tan precipitate that is recovered by filtration and suction.

The tan precipitate, bis 2,4-dichlorophenoxyacetate, is preferably dried, under vacuum at a presaure of about 5 mm. pressure and at a temperature of between about 70° and 90° C. and preferably between 80° and 90° C. with best results at 80° C. The filtrate contains 1 mole of ammonium sulfate and 1 mole of potassium sulfate that can be recovered by drying and can be subsequently used as an agricultural fertilizer.

In preparing the compounds of this invention, other halogenated phenoxyalkanoic acids can be substituted for the 2,4-dichlorophenoxyacetic acid, including, for example, p-chlorophenoxyacetic acid, 2,4,5-trichlorophenoxypropionic acid, 2,3,4,5,6-pentachlorophenoxypropionic acid, 2,3,5,6-tetrachlorophenoxyacetic acid, forming respectively, bis p-chlorophenoxyacetate, bis 2,4,5-trichlorophenoxypropionate, bis 2,3,4,5,6-pentachlorophenoxypropionate and bis 2,3,5,6-tetrachlorophenoxyacetate,

COMPOSITIONS

The compounds of the present invention can be present in combination with at least one inert carrier, said compounds preferably being present in a herbicidal amount. Thus, the compounds of the present invention can be uniformly admixed with any of the well known free-flowing particulate dry inert solid carriers which may be organic or inorganic. These inert carriers include, for example, sawdust, the flour derived from soybeans, tobacco, walnut shell, wheat, wood by-products, lignin and lignocellulose, ligninsulfonic acid, cork, urea-formaldehyde, resins, silicas, carbonates, calcite, dolomite, silicates, tricalcium phosphate, boric acid, etc. The amount of active ingredient present being determined by the usefulness of the product.

In addition, the compositions may optionally contain from about 0.5 to about 1.0 weight percent of a surfactant or wetting agent, which renders the products wettable and dispersable, thereby facilitating the application thereof in the field.

The ingredients may be simply mixed together thoroughly with said inert carrier or blended and then passed through a high-speed grinder, after which the mixture is a free flowing product.

The surfactants disclosed in Bulletin E-607 of the Bureau of Entomology and Plant Quarantine of the United States Department of Agriculture, or surface active agents disclosed in U.S. Pat. Nos. 2,426,417; 2,655,447; 2,412,510 and 2,139,276, are suitable for use in the practice of this invention.

Examples of suitable formulations include the following:

EXAMPLE ONE

Three pounds of a composition in the form of a 325 mesh powder and containing the following ingredients:

|  | By weight: |
|---|---|
| Bis 2,4-dichlorophenoxyacetate | 40% |
| Surfactant (Dupanol C) | 1% |
| Diatomaceous earth (Attaclay) | 59% | was added to 100 gallons of water. This aqueous composition will control the following weeds present with sugarcane: spiny amaranth, carpetweed, geranium, cressleafed groundsel, common lambsquarter, mexicantea, pellitoryweed, common purslane, ragweed, sowthistel and toadflax.

EXAMPLE TWO

Field corn was planted in 3 foot square flats wherein the seeds were equally spaced at 4 inch intervals. After planting, the surface of each flat was dusted with 9.4 gms. of a powder composition containing the following:

|  | By weight: |
|---|---|
| Bis 2,4-dichlorophenoxyacetate | 10% |
| Surfactant (Dupanol C) | 1% |
| Diatomaceous earth (Attaclay) | 89%. |

The ingredients were initially mixed in a ribbon type blender and are thereafter passed through a high speed grinder to form a smooth, 325 mesh powder.

The corn germination was ninety-two percent on three replicated flats while there were no broad leaf weeds observed in the flats.

EXAMPLE THREE

Thirty pounds of bis 2,4-dichlorophenoxyacetate was dusted on one acre of a canal heavily infested with underwater growth. Hydrilla, coontail, watermillfoil, waterlilly, pondweed and naiad were each observed as being successfully controlled at the end of a three-week period. No ill effect upon aquatic life was observed.

EXAMPLE FOUR

A liquid composition was prepared by dissolving 2,722 gms., of bis 2,4-dichlorophenoxyacetate in 1,000 gms. of a 50 percent solution of ethylenediamine in water. Forty grams of surfactant, amine salt of a higher secondary alkyl sulfate, was added thereto, with agitation. Water was added to make one gallon. One quart of this composition, when added to 100 gallons of water and sprayed upon an acre of uncultivated raw land, controls the following weeds; bindweed, bullthistle, chickweed, cockleburr, dogfennel, duckweed, elderberry, morning glory, mustard, pigweed, purslane, sowthistle, spiny amaranth, stinkweed, thistles, virginia creeper and wild garlic.

EXAMPLE FIVE

Two moles of 2,4-dichlorophenoxyacetic acid were dissolved in 1,000 ml. of water containing 2 moles of potassium hydroxide. One mole of ammonium persulfate was then dissolved in another 1,000 ml. of water and then the 2 aqueous solutions were admixed with each other. Instead of filtering the precipitated bis 2,4-dichlorophenoxyacetate, the total reaction product was vacuum dried within the temperature range of 70° to 90° C. and at about 5 mm. Hg. of pressure. The yield was 725 gms. which is 97% of the theoretical yield. The anhydrous product produced consists of bis 2,4-dichlorophenoxyacetate, ammonium sulfate and potassium sulfate, said homogenous mixture thereafter being passed through a high speed grinder to produce a free flowing powder.

EXAMPLE SIX

The homogenous mixture as prepared in Example Five is added to 6,525 gms. of talc and ground in a ball mill for eight hours resulting in the formation of a fine free flowing powder. This powder was used to cover the surface of the furrow when corn was being cultivated. The powder covered about an acre and a half. Unexpectedly, the weeds in this treated area were controlled and the small amount of fertilizer was beneficial to the corn.

What is claimed is:

1. A compound useful as a plant growth regulator and having the formula:

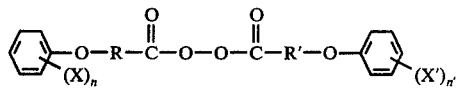

wherein X and X' are each chlorine atoms, R and R' are each alkyl groups containing from 1 to 4 carbon atoms and n and n' each have a value from 1 to 5.

2. The compound of claim 1 wherein R and R' are each methyl or ethyl.

3. The compound of claim 1 wherein R and R' are each methyl, and n and n' each have a value of 2.

4. The compound of claim 1 wherein R and R' are each ethyl, and n and n' each have a value of 2.